(12) United States Patent
Brunnen et al.

(10) Patent No.: US 7,766,821 B2
(45) Date of Patent: Aug. 3, 2010

(54) BENDABLE PORTION OF AN INSERTION TUBE OF AN ENDOSCOPE AND METHOD OF PRODUCING IT

(75) Inventors: Rainer Dirk Brunnen, Seitingen-Oberflacht (DE); Thomas Jurgen Simon, Emmingen (DE)

(73) Assignee: Henke-Sass, Wolf GmbH, Tuttlingen (DE)

( * ) Notice: Subject to any disclaimer, the term of this patent is extended or adjusted under 35 U.S.C. 154(b) by 1234 days.

(21) Appl. No.: 11/148,036

(22) Filed: Jun. 8, 2005

(65) Prior Publication Data

US 2005/0272978 A1    Dec. 8, 2005

(30) Foreign Application Priority Data

Jun. 8, 2004    (DE) ................. 10 2004 027 850

(51) Int. Cl.
*A61B 1/00*    (2006.01)
(52) U.S. Cl. ............... 600/142; 600/139; 600/141
(58) Field of Classification Search ........ 600/129, 600/139, 141–146
See application file for complete search history.

(56) References Cited

U.S. PATENT DOCUMENTS

| | | | |
|---|---|---|---|
| 2,515,366 A | 7/1950 | Zublin | |
| 3,557,780 A | 1/1971 | Sato | |
| 3,583,393 A | 6/1971 | Takahashi | |
| 3,739,770 A | 6/1973 | Mori | |
| 3,998,216 A | 12/1976 | Hosono | |
| 4,108,211 A | 8/1978 | Tanaka | |
| 4,834,069 A | 5/1989 | Umeda | |
| 5,152,744 A | 10/1992 | Krause et al. | |
| 5,178,129 A * | 1/1993 | Chikama et al. | ............ 600/142 |
| 5,394,864 A | 3/1995 | Kobayashi et al. | |
| 5,448,989 A | 9/1995 | Heckele | |
| 5,749,828 A * | 5/1998 | Solomon et al. | ............ 600/141 |

(Continued)

FOREIGN PATENT DOCUMENTS

DE    6938905    1/1970

(Continued)

OTHER PUBLICATIONS

"Development of Three-dimensional (3D) laser cutting" Laser Technology, vol. 22, No. 6, Dec. 1998, pp. 352-256.

*Primary Examiner*—Linda C Dvorak
*Assistant Examiner*—Alireza Nia
(74) *Attorney, Agent, or Firm*—Patterson, Thuente, Skaar & Christensen, P.A.

(57) ABSTRACT

A bendable portion, which is arranged at the distal end of an insertion tube of an endoscope, comprises a plurality of tube segments, each of said tube segments having connecting means that cooperate with the connecting means of the adjacent tube segment, as well as control wires that can control the bending of the bendable portion. The respective connecting means of a tube segment are provided such that they axially protrude from the faces of the tube segment and are located within the mantle of the tube segment and such that they do not exceed the thickness of the mantle. The connecting means, which are provided on the respective faces of adjacent tube segments and which are located opposite each other, complement each other in the manner of a hinge-type connection.

7 Claims, 12 Drawing Sheets

U.S. PATENT DOCUMENTS

| | | | |
|---|---|---|---|
| 5,785,806 A * | 7/1998 | Engle et al. | 156/580.2 |
| 5,807,241 A * | 9/1998 | Heimberger | 600/142 |
| 6,364,828 B1 * | 4/2002 | Yeung et al. | 600/142 |
| 6,641,528 B2 | 11/2003 | Torii | |

FOREIGN PATENT DOCUMENTS

| | | |
|---|---|---|
| DE | 4222121 | 9/1993 |
| DE | 195 35 179 A1 | 3/1997 |
| DE | 101 13 713 C1 | 12/2002 |
| EP | 0 626 604 A2 | 11/1994 |
| EP | 0626604 | 11/1994 |
| EP | 0439931 | 3/1995 |
| EP | 0 782 836 A1 | 7/1997 |
| EP | 1090581 | 12/2003 |
| WO | WO 97/03611 | 2/1997 |

* cited by examiner

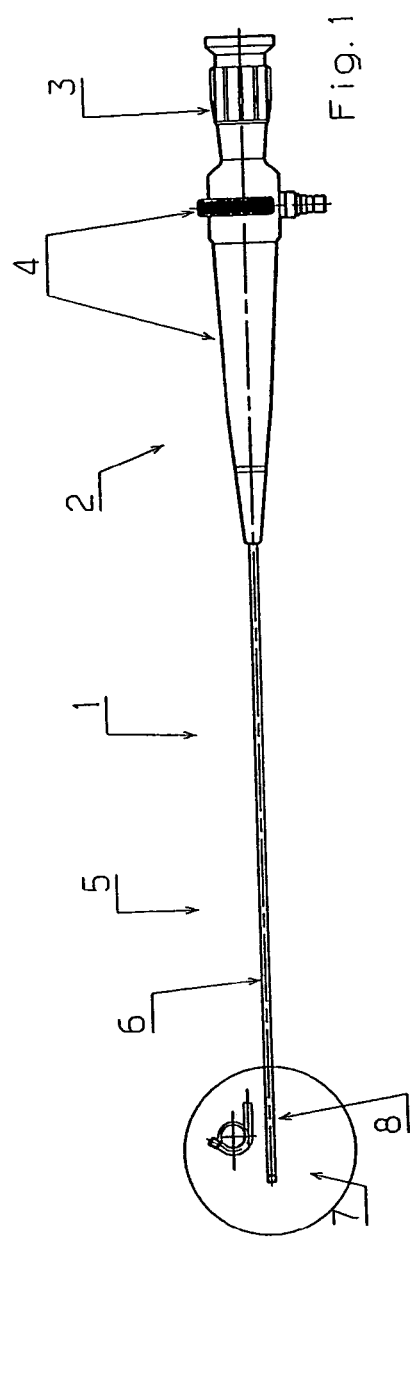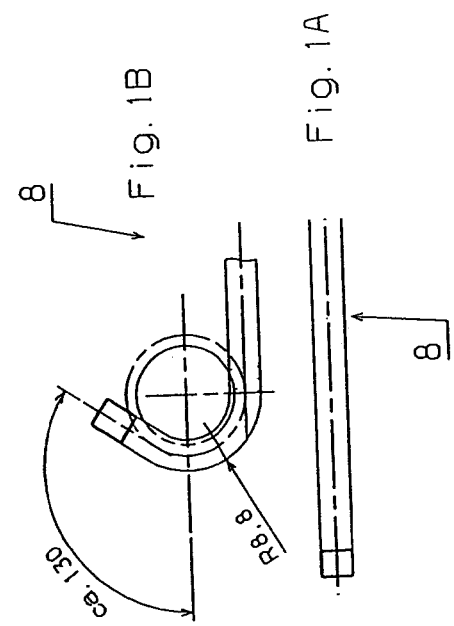

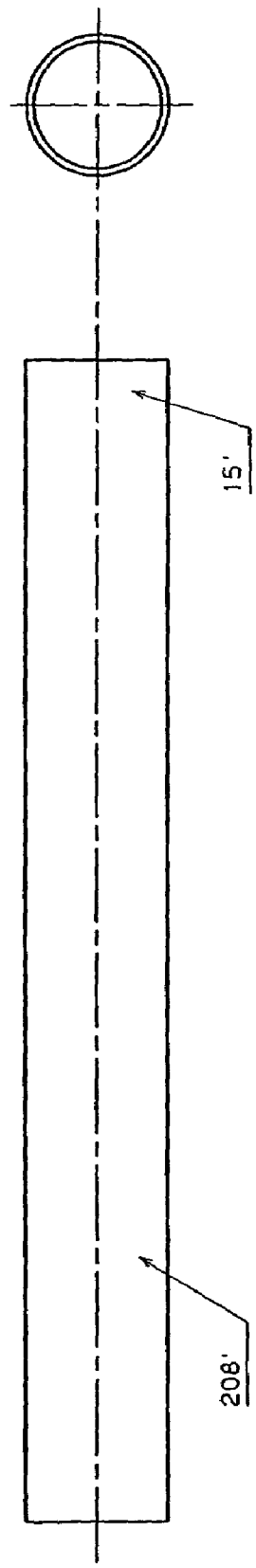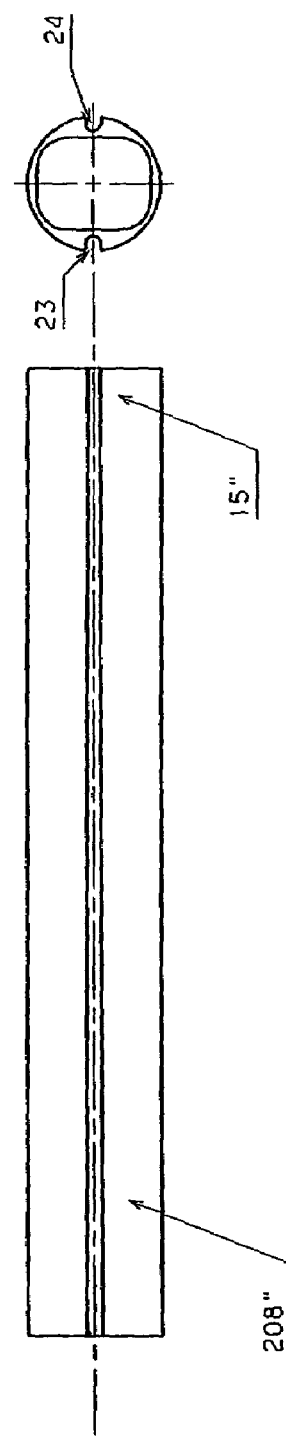

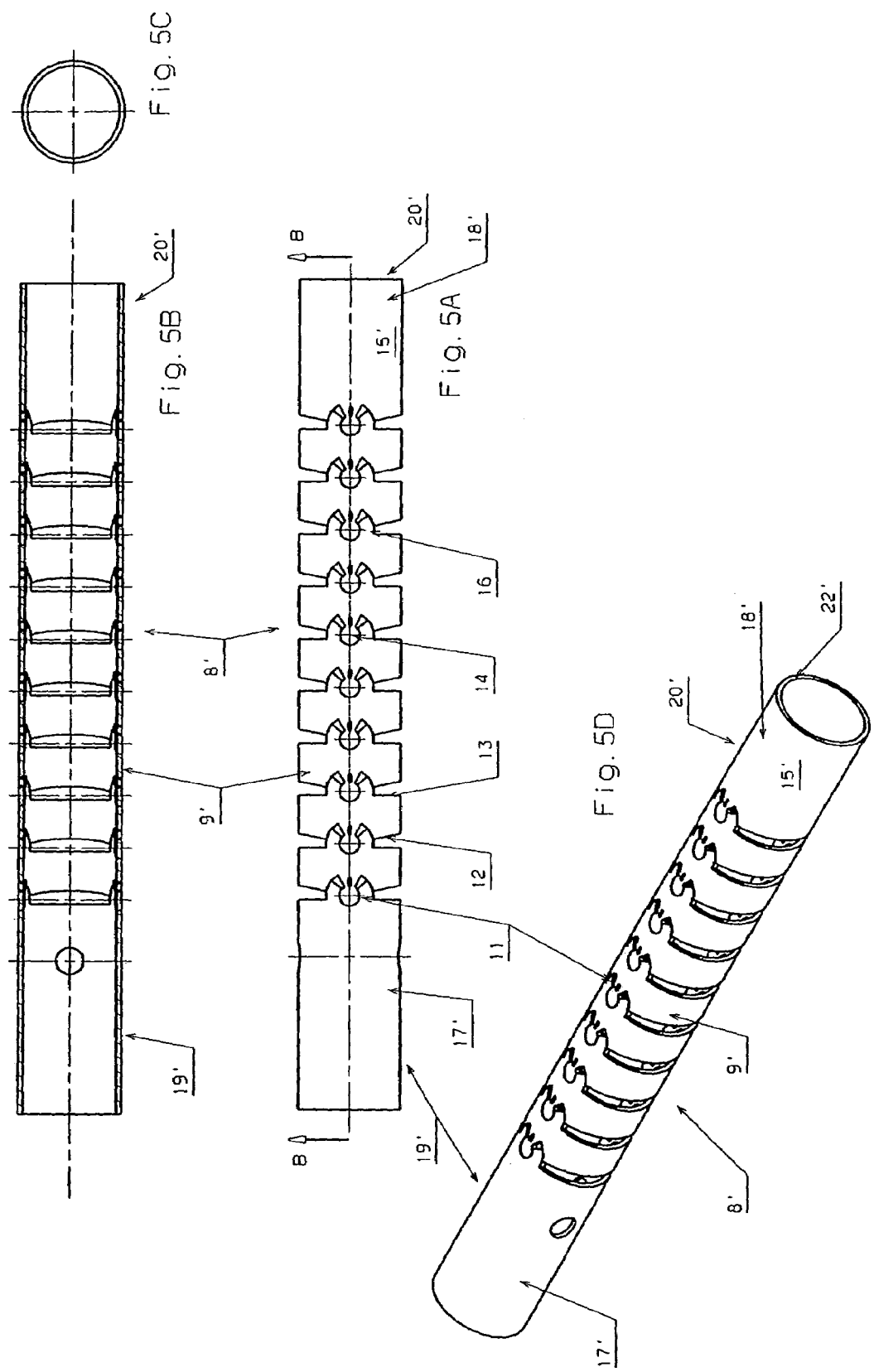

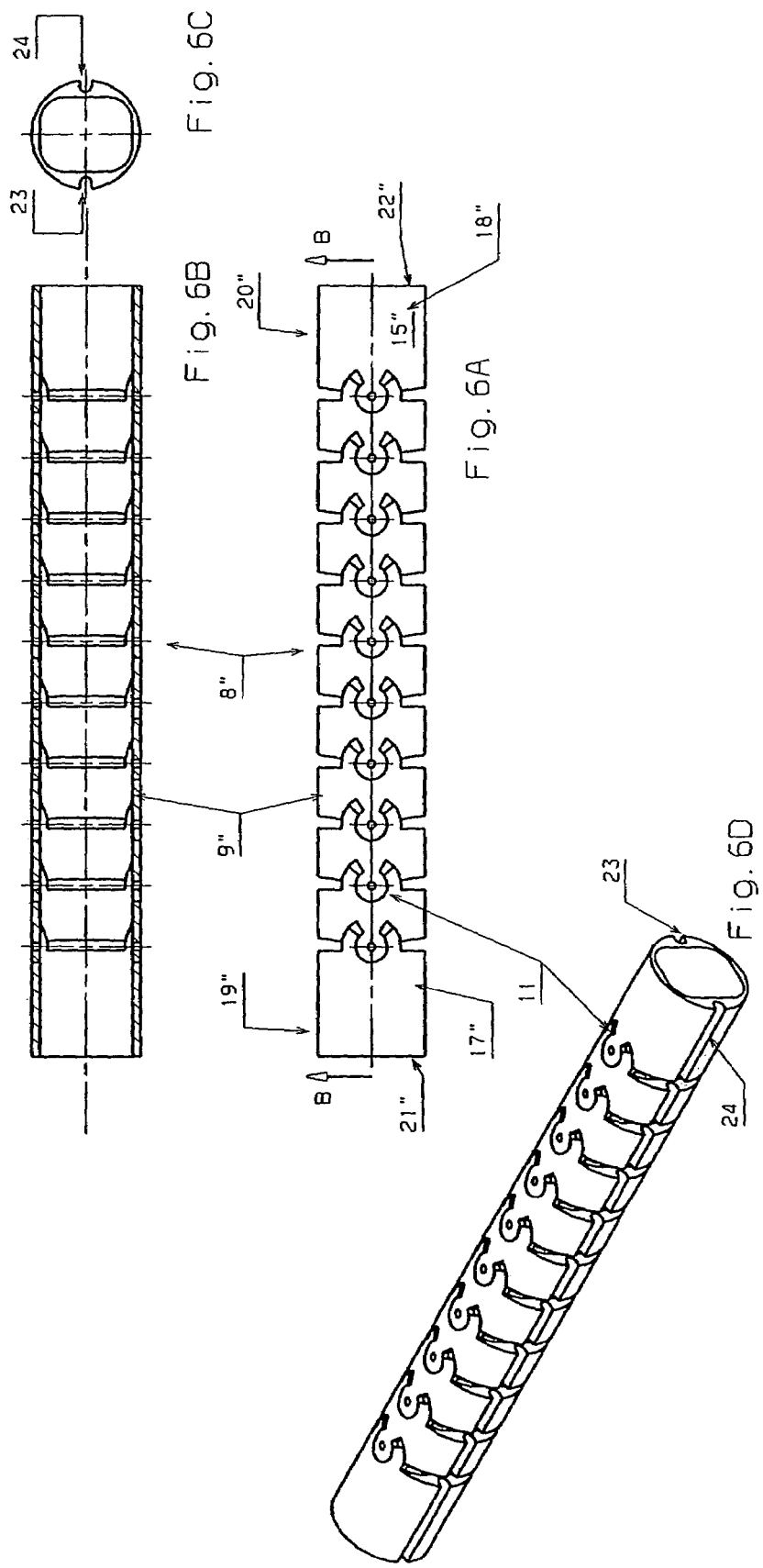

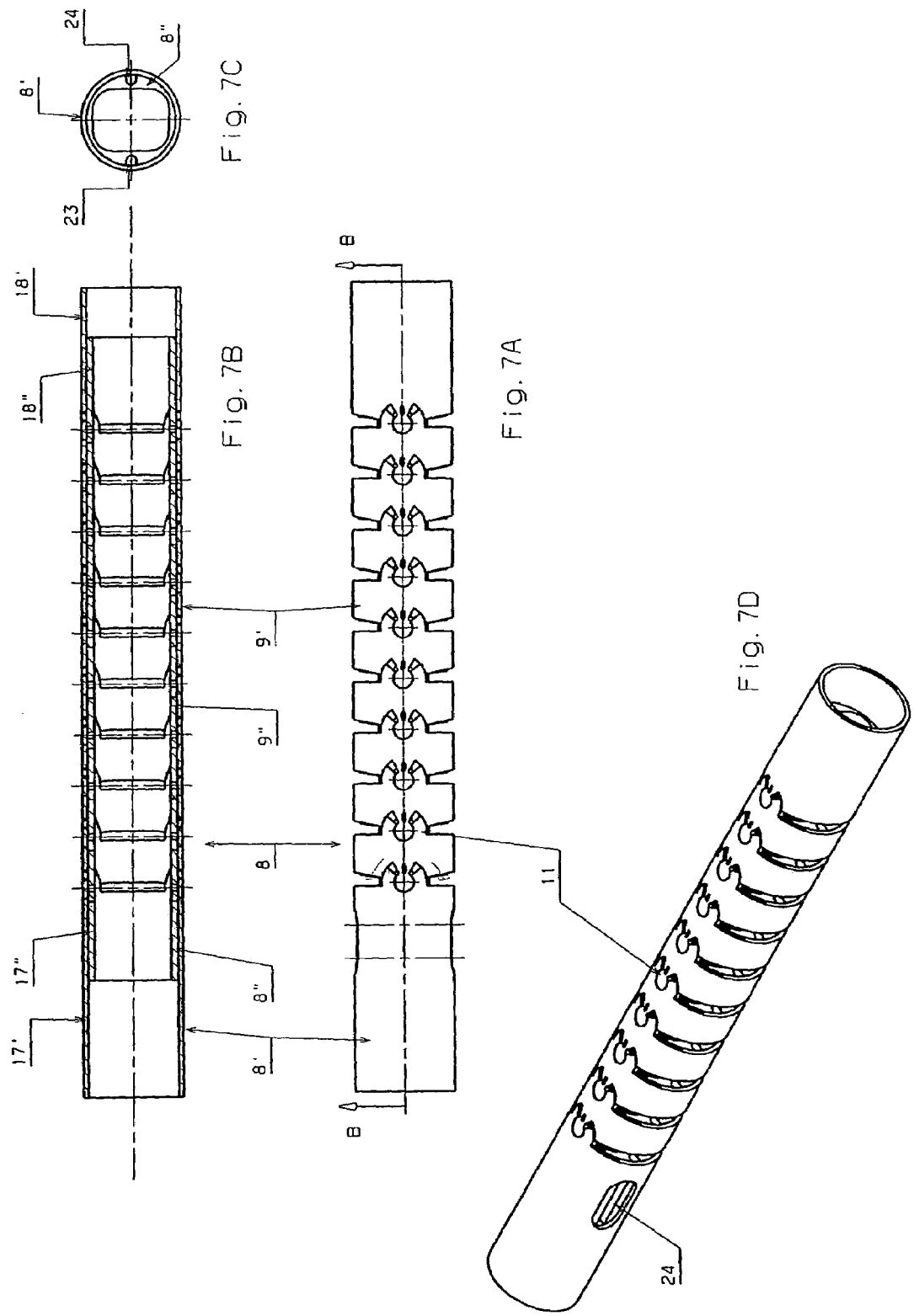

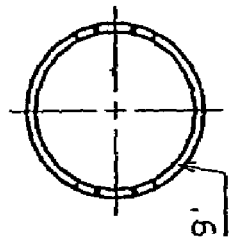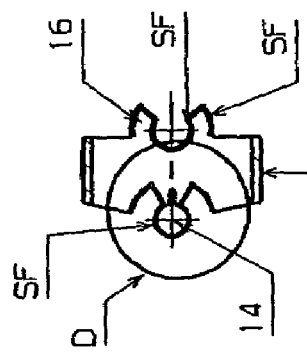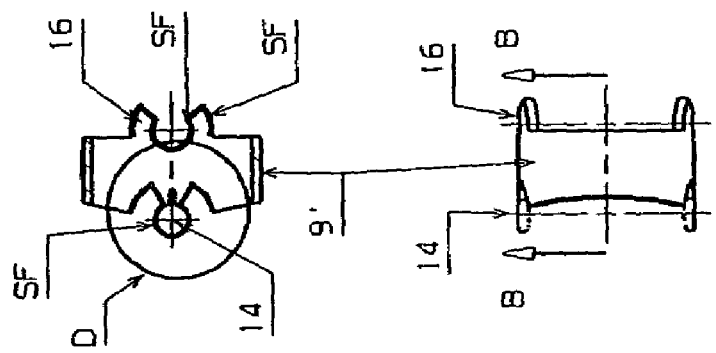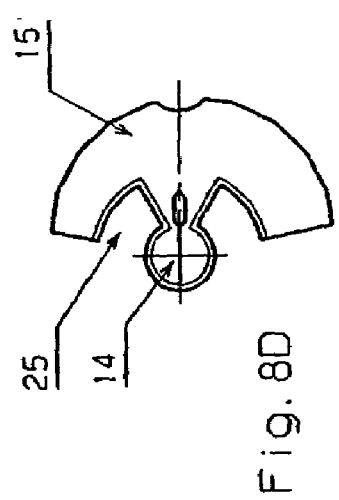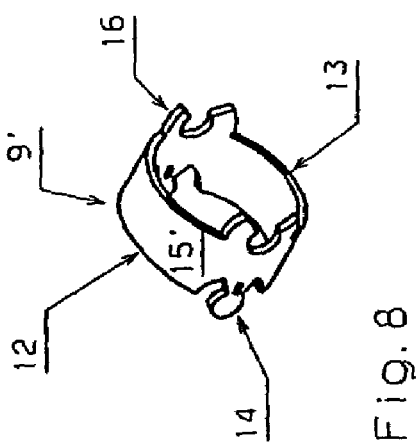
Fig. 8C
Fig. 8A
Fig. 8B
Fig. 8D
Fig. 8

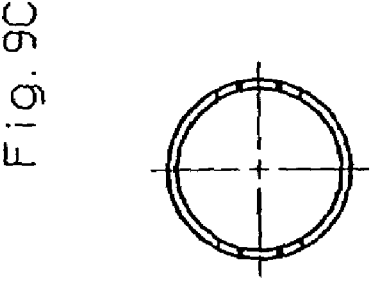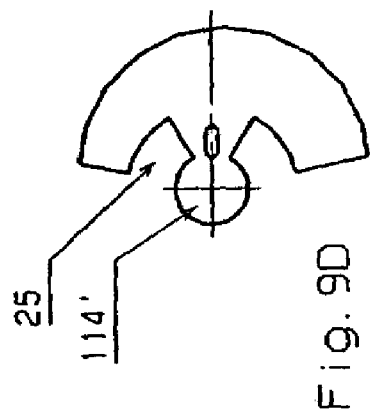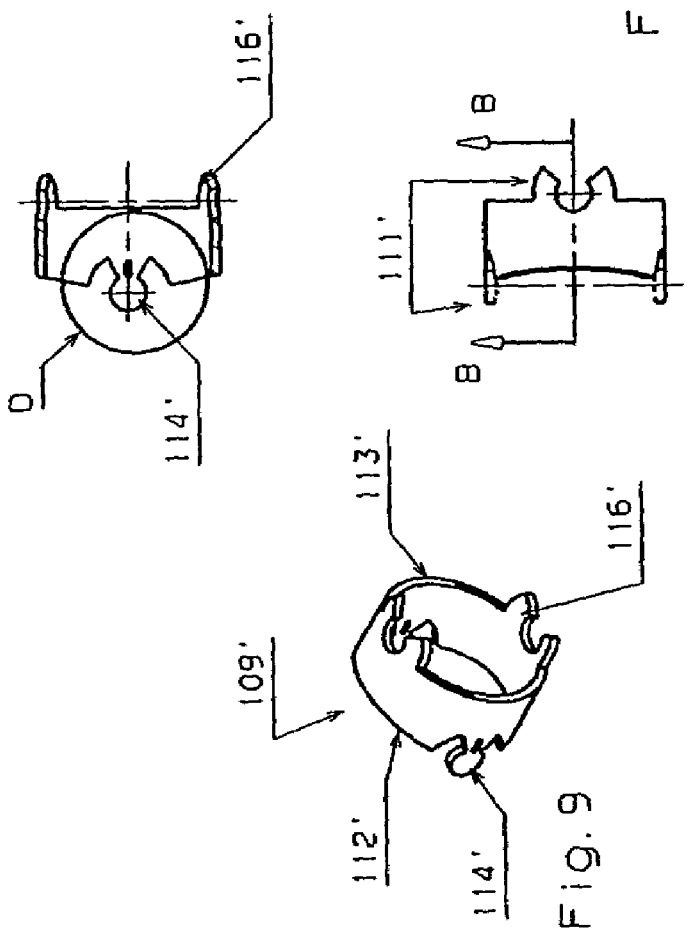

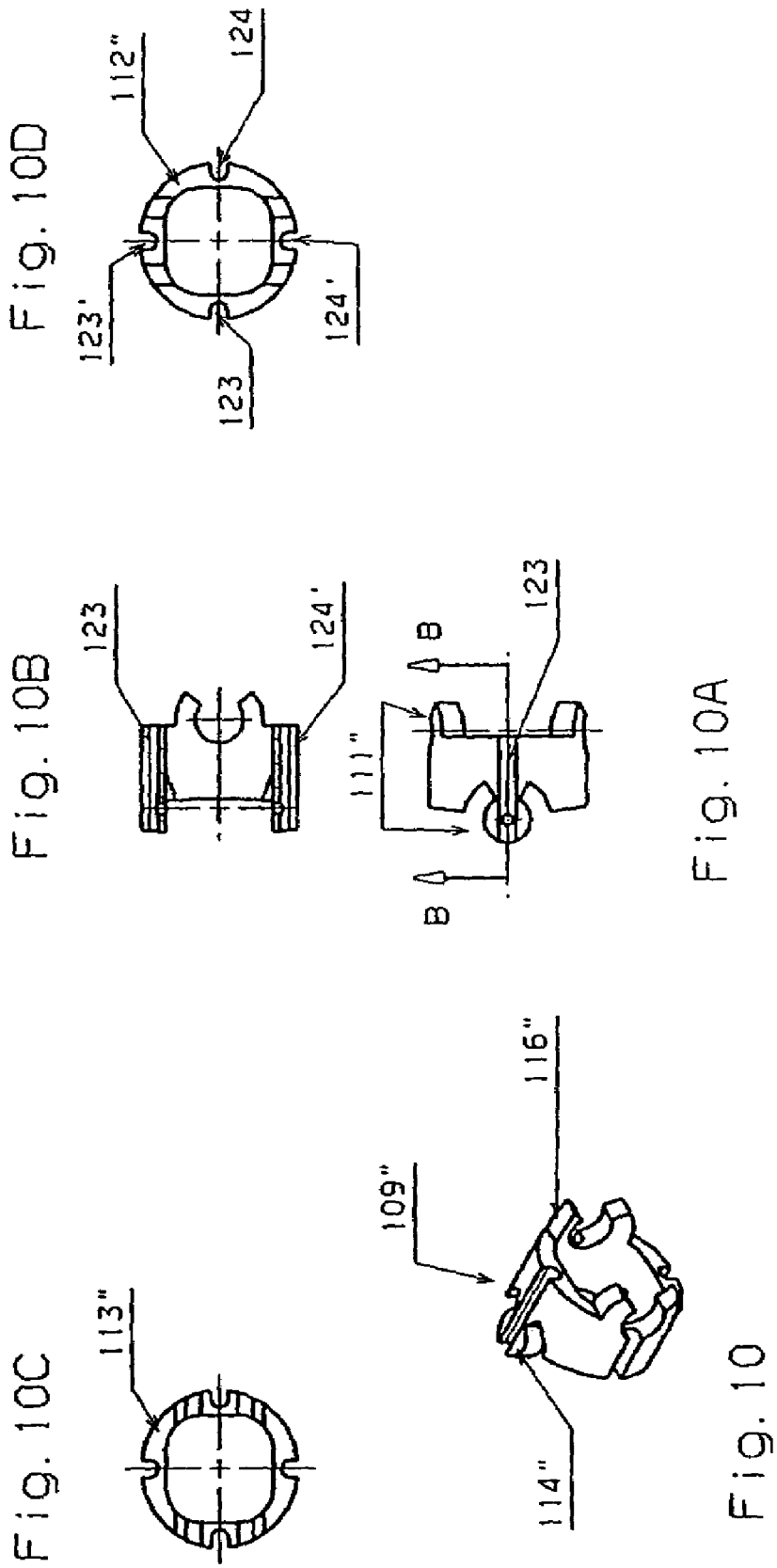

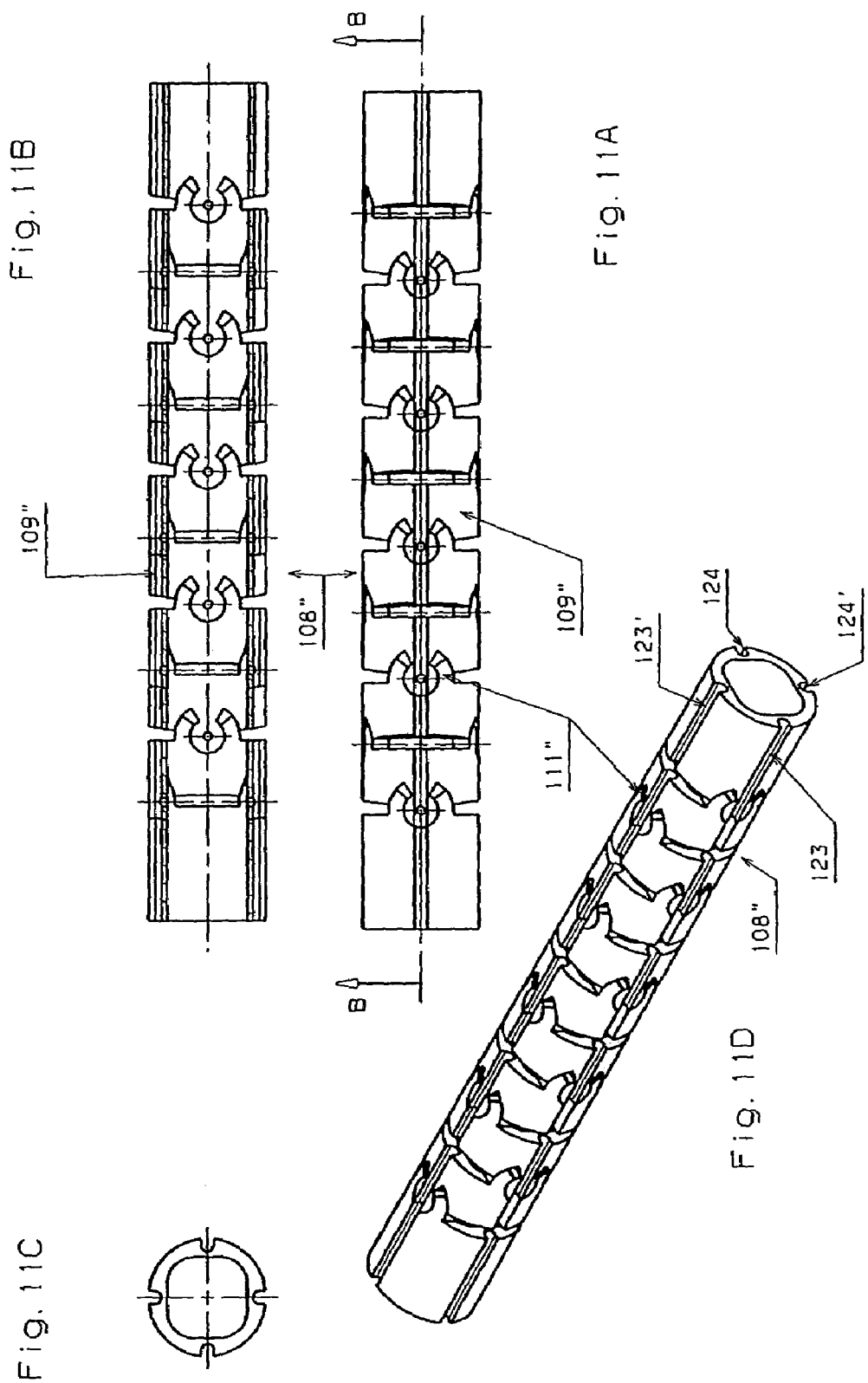

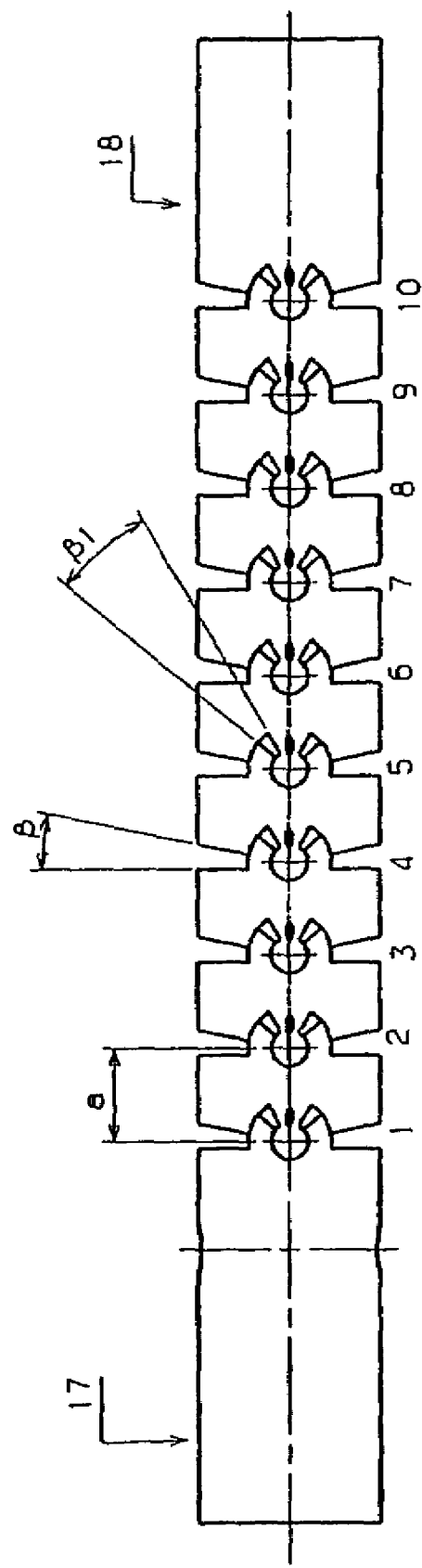

BENDABLE PORTION OF AN INSERTION TUBE OF AN ENDOSCOPE AND METHOD OF PRODUCING IT

The current application claims the benefit of priority to German Patent Application No. DE 10 2004 027 850.4-55 filed on Jun. 8, 2004. Said application is incorporated by reference herein.

FIELD OF THE INVENTION

The invention relates to a bendable portion arranged at the distal end of an insertion tube of an endoscope, said bendable portion comprising a plurality of tube segments, each of which comprises a connecting portion that cooperates with the connecting portion of the adjacent tube segment, as well as control wires that control the bending of the bendable portion. The invention further relates to a method of producing such a bendable portion.

BACKGROUND OF THE INVENTION

Endoscopes comprising such bendable and controllable portions at the distal ends of their insertion tube are described in a great number of references, some of which shall be discussed in more detail below, such as DE 101 43 966 A1, DE 42 34 833 A1, EP 0 439 931 B1 and EP 1 090 581 B1.

All of these cited references show bendable portions that are each provided at the distal ends of an insertion tube of an endoscope. Said insertion tube may be rigid or flexible. However, an essential property of the bendable portion of the insertion tube is that it is controllable with regard to its bending direction, via control wires integrated in the insertion tube.

EP 1 090 581 B1 describes a bendable portion which comprises two control wires, i.e. the bendable portion is bendable only in one plane, whereas the other aforementioned references show bendable portions comprising four control wires each, allowing the bendable portion to be bent in two planes and, thus, allowing spatial bending.

All these known bendable portions consist of a plurality of connecting rings or joint rings, respectively, or, more generally speaking, of tube segments which are connected with each other via connecting means allowing them to be pivoted relative to each other, said connecting means each being respectively arranged on the faces of the tube segments.

Now, the arrangement of the connecting means on the respective faces of the individual tube segments depends on whether the bendable portion is to be bendable only in one plane, or whether it is to be spatially bendable, i.e. in two planes. If the bendable portion is to be bendable only in one plane, as represented in EP 1 090 581 B1, there are two connecting means arranged on each face, i.e. as seen in the distal and proximal directions, said connecting parts being Located opposite each other, with a circumferential offset of 180°. The pivot axes of these connecting means on the individual tube segments respectively extend, as seen in an axial direction, on a continuous surface line.

However, if the bendable portion is to be spatially bendable, the individual tube segments need to be pivotable relative to each other also in a second plane, which is staggered 90° to the first plane. This requires the connecting means which are respectively arranged on the faces of a tube segment to be offset 90° relative to each other, as is evident, for example, from EP 0 439 931 B1. In order to also allow control of this spatial bending, there are provided, of course, four control wires, which are circumferentially offset 90° relative to each other.

The connecting means are provided as lugs, which protrude from the respective faces of the tube segments and are, for example, provided with bores into which bolts are inserted which extend radially inwardly. This means that these connecting means, especially the lug-shaped protrusions, need to overlap and, therefore, are bent outwardly or inwardly from the surface of the tube segments. However, these connecting means, and also the bolts arranged therein, then protrude beyond the outer and/or inner periphery of the bendable portion, but in particular, the bolts protrude into the interior space of the bendable portion.

The control wires are thus guided inside the bendable portion, namely, as shown in DE 42 34 833 A1 and EP 1 090 581 B1, in guides which are provided on the inner surfaces of individual tube segments. In both DE 101 43 966 A1 and EP 0 439 931 B1, such guides are provided directly at the bolt heads of the connecting means protruding into the interior space, in a manner similar to eye rings.

What all these known bendable portions have in common is that they consist of tube segments and of connecting parts, which are extremely complex with regard to their production, but especially also in respect of their mounting.

As a result, there is a need for bendable portions that substantially solves the innate drawbacks and restrictions presented with these conventional concepts and designs.

SUMMARY OF THE INVENTION

It is therefore an object of the present invention to substantially simplify this production and mounting process, as well as to provide the interior space of the bendable portion to have a smooth wall and to be free from projections.

It is also another object of the present invention to provide the interior space free from control wires which would otherwise obstruct the incorporation of lighting means, which are also required, such as glass fiber cords and electrical lines for the optical unit and the sensor unit, at the distal end of the bendable portion. In particular, however, the interior space should also be kept free for installations which are required for rinsing and suction operations and, as the case may be, for operative tools acting at the distal end.

Still another object of the present invention is to provide a method of producing such bendable portion from a given bending-resistant tube, said method making it possible that the individual tube segments with their connecting means no longer need to be assembled by using further connecting means, e.g. bolts and rivets, etc., but are ready-to-use and suitable for further use in one single process step, as it were.

These objects are inventively achieved by a bendable portion of the aforementioned type in that the respective connecting means of a tube segment are provided to axially protrude from the faces of said tube segment and to be arranged within the mantle of the tube segment and in that they do not exceed the thickness of the mantle, with the connecting means provided on the respective faces of adjacent tube segments and located opposite each other complementing each other in the manner of a hinge-shaped connection.

These connecting means according to the invention protrude neither outwardly nor inwardly beyond the outer or, respectively, the inner surface of the tube segments, and also, no additional means are provided to hold the connecting means together so as to form protrusions. Thus, means in the form of bolts and/or rivets, which form radially directed pivot axes and pivotably connect the respective connecting means with each other, can be omitted. Rather, the connecting means are provided within the mantle thickness of the tube segments and extend into each other in an axial direction and are pivotable relative to each other. This design according to the invention will ensure that both the outer and the inner surfaces of the tube segments, and, thus, in particular, the interior space of the bendable portion, will have no protrusions, thus producing smooth outer and inner surfaces.

In another embodiment of the present invention, the connecting means provided on one face of a tube segment are designed in the manner of a pin directed and protruding toward the face of an adjacent tube segment, and the connecting means arranged on the other face of the tube segment are provided as claws embracing the pin of an adjacent tube segment, both the pin and the claws being part of the mantle of the respective tube segment.

This above-described design of the connecting parts allows a connection to be established, which holds the tube segments together and is, at the same time, pivotable, without having to use additional means in the form of bolts or the like. The claw-shaped connecting means form, as it were, a clamp for the pin-shaped connecting means of the other tube segment, so that a connection holding the tube segments together is established without having to use an additional, separate part as connecting means.

The connecting means respectively arranged on one of the faces of a tube segment are advantageously provided either as pins or as claws, in which case the connecting means provided on the other face of the same tube segment are, on the other hand, provided either as claws or as pins.

According to this embodiment, the connecting means which are respectively provided on a specific face of a tube segment and which, as mentioned, are located opposite each other with a circumferential offset of 180° relative to each other, are identical in design and so are the corresponding pin- or claw-shaped connecting means on the face of another tube segment located opposite such face of a tube segment. This respectively identical design of the connecting means on the same face of a tube segment simplifies the production of such tube segments.

In an embodiment according to the present invention, the pin arranged on the face of a tube segment is provided in the manner of a circular disk, and the claws arranged on the face of the adjacent tube segment enclose a circular recess between them, which recess corresponds to the dimensions of the circular disk-shaped pin, said claws receiving the pin in said recess.

Such design of the connecting means ensures that they are within the dimensions of the mantle of the tube segment and, in particular, ensures that the claws cannot be pulled off the pin both in axial and in radial directions.

In a further advantageous embodiment of the present invention, the first tube segment at the proximal end of the bendable portion and the last tube segment at the distal end of the bendable portion respectively have no pin- and/or claw-type connecting means on their faces forming the ends of the bendable tube portion.

These respective first and last tube segments of the bendable portion are each designed according to their respective purposes. Thus, the last tube segment at the distal end of the bendable portion is intended to receive optics and a sensor etc. and, in particular, to be inserted into a body cavity. Therefore, it is subject to a special design. The same goes for the tube segment provided at the proximal end of the bendable portion, which segment is connected in a special way, not described herein, to the proximal part of the tubular insertion tube of the endoscope.

In order to achieve the objects of the present invention, the bendable portion, which is hereinafter always referred to as outer bendable portion, has inserted therein a second, inner bendable portion, which is of identical design as regards the number of tube segments and the arrangement of the connecting parts on said tube segments, and whose outer diameter is adapted to the inner diameter of the outer bendable portion such that the inner bendable portion is slidable into the outer bendable portion, said inner bendable portion comprising at least two grooves in its outer peripheral surface, which have a circumferential offset of 180° relative to each other and extend in an axial direction over the individual tube segments, said grooves each having a control wire guided therein and both of said grooves being arranged with a circumferential offset of 90° relative to the connecting means.

The particular design of the bendable portion in a double-walled form, as it were, with the grooves formed in the outer peripheral surface of the inner bendable portion, provides secure guiding of the control wires. At the same time, this has the effect that the interior space of the double-walled bendable portion, i.e. in particular the interior space of the inner bendable portion, remains free from wire ropes, which greatly facilitates insertion of other flexible tubes, electrical lines, etc. Also, the incorporation of the wire ropes into the double-walled bendable portion is relatively easy, because the wire ropes need not be passed through or threaded into eye-shaped guides. Rather, the wire ropes can already be placed in the respective grooves when sliding the inner bendable portion into the outer bendable portion and can be installed in one operation, but, on the other hand, it may also be slid into the grooves only after assembly of the outer and inner bendable portions.

Due to the outer peripheral surface of the inner bendable portion being in close contact with the inner peripheral surface, the grooves, together with the inner peripheral surface of the outer bendable portion, form a closed, channel-shaped guide in which the wire ropes can slide without jamming.

In a specific embodiment, four axially extending grooves are provided on the outer peripheral surface of the inner bendable portion, which grooves have a circumferential offset of 90° relative to each other, and at the same time, the connecting parts arranged in pairs on the respective faces of the tube segments also have an offset of 90° relative to each other.

The provision of four wire ropes is required if the bendable portion is to be bendable in two planes, i.e. spatially bendable. However, at the same time, the connecting means then also have to be arranged, in respectively alternating fashion, with a circumferential offset of 90° relative to each other on the respective tube segments in order to allow spatial bending of the bendable portion.

In order to prevent the inner and outer bendable portions inserted into each other from being displaced relative to each other, which might prevent or at least impair the bendability or pivotability of the respective tube segments relative to each other, the individual tube segments of the inner and outer portions are each fixed to one another by spot welding, once they are located exactly opposite each other, i.e. with complete congruence of the bendable portions established.

Such spot welding is easy to perform and guarantees that the respective bendable portions remain fixed relative to each other.

In order to achieve objects of the present invention, there is provided a method of producing a bendable portion comprising a multiplicity of tube segments which are arranged in a row and are connected to each other via connecting parts so as to be pivotable relative to each other, said method comprising the steps of:

a) providing a bending-resistant tube which has dimensions that correspond to the desired dimensions of the bendable portion;

b) providing a laser-cutting device;

c) placing the bending-resistant tube in the laser-cutting device;

d) guiding the laser beam of the laser-cutting device according to the cutting lines predetermined by the configuration of the tube segments and by the respective connecting means, with the laser beam always being radially directed to the tube, and e) breaking away the wall parts cut out of the bending-resistant tube, so as to enable pivotability of the individual tube segments relative to each other.

Due to the special, above-described design of the connecting means of the individual tube segments, it is possible to carry out the method according to the invention and to cut the bendable portion out of a bending-resistant tube in one single cutting process. For this purpose, the person skilled in the art will select a laser beam of suitable thickness to ensure the faultless function of the connecting means, in particular their pivotability. After the cutting process, the bendable portion is already usable and may be incorporated into the endoscope to be produced. This method according to the invention avoids, in particular, the above-described, cumbersome assembly process in which individual tube segments have to be connected to each other by additional connecting means, such as bolts, pins, rivets, or the like.

In an advantageous embodiment of the above-described method, the bending-resistant tube is rotated and/or axially displaced under the stationary laser beam in the cutting device.

This manner of carrying out said method allows a simpler construction of the laser-cutting device.

Finally, in a further advantageous manner, the wall parts cut out of the tube can be broken out of the tube by ultrasonic means.

This method has the advantage that no mechanically operating tools need to be employed.

BRIEF DESCRIPTION OF THE DRAWINGS

In the following, the inventive bendable portion of an insertion tube of an endoscope is described in greater detail using exemplary embodiments. The corresponding figures show:

FIG. 1 shows a lateral view of an endoscope, in particular a nasopharyngoscope;

FIG. 1A shows a slightly enlarged view of the distal end of an insertion tube;

FIG. 1B shows a view of the distal end of FIG. 1A in a position bent approximately 125°;

FIG. 3 shows a view of a bending-resistant tube before turning it into an outer bendable portion of the insertion tube;

FIG. 3A shows an end view of the bending-resistant tube of FIG. 3;

FIG. 4 shows a view of a bending-resistant tube before turning it into an inner bendable portion of the insertion tube;

FIG. 4A shows an end view of the bending-resistant tube of FIG. 4;

FIG. 5A shows a top view of the outer bendable portion;

FIG. 5B shows a longitudinal section along the line B-B of FIG. 5A;

FIG. 5C shows a front view of the outer bendable portion;

FIG. 5D shows a perspective lateral view of the outer bendable portion of FIG. 5A;

FIG. 6A shows a top view of the inner bendable portion of the insertion tube;

FIG. 6B shows a sectional view of the inner bendable portion along the line B-B of FIG. 6A;

FIG. 6C shows a front view of the inner bendable portion;

FIG. 6D shows a perspective lateral view of the inner bendable portion of FIG. 6A;

FIG. 7A shows a top view of the bendable distal end of the insertion tube, consisting of the outer and inner bendable portions;

FIG. 7B shows a sectional view of the bendable distal end along the line B-B of FIG. 7A;

FIG. 7C shows a front view of the bendable distal end comprising the outer and inner bendable portions;

FIG. 7D shows a perspective lateral view of the bendable distal end of FIG. 7A;

FIG. 8 shows a perspective view of an individual tube segment of the outer bendable portion;

FIG. 8A shows a top view of the tube segment of FIG. 8;

FIG. 8B shows a sectional view of the tube segment along the line B-B of FIG. 8A;

FIG. 8C shows a front view of the tube segment;

FIG. 8D shows an enlarged view of detail D of FIG. 8B;

FIG. 9 shows a perspective lateral view of a tube segment of the outer portion, wherein the connecting means are arranged on a first face with an offset of 90° relative to the connecting means on the other face;

FIG. 9A shows a top view of the tube segment of FIG. 9;

FIG. 9B shows a section of the tube segment along the line B-B of FIG. 9A;

FIG. 9C shows a front view of the tube segment;

FIG. 9D shows an enlarged view of detail D of FIG. 9B;

FIG. 10 shows a perspective lateral view of a tube segment of the inner bendable portion with a corresponding arrangement of the connecting means of FIG. 9, which are offset relative to each other;

FIG. 10A shows a top view of the tube segment of FIG. 10;

FIG. 10B shows a sectional view of the tube segment along the line B-B of FIG. 10A;

FIG. 10C shows a front view of the tube segment;

FIG. 10D shows a view of the opposite face of the tube segment;

FIG. 11A shows a top view of an inner bendable portion for four wire ropes;

FIG. 11B shows a section of the inner bendable portion along the line B-B of FIG. 11A;

FIG. 11C shows a front view of the inner bendable portion;

FIG. 11D shows a perspective lateral view of the inner bendable portion for four wire ropes;

FIG. 14 shows a bendable portion with indications of distances and angles.

DETAILED DESCRIPTION OF THE INVENTION

Figure 2A:
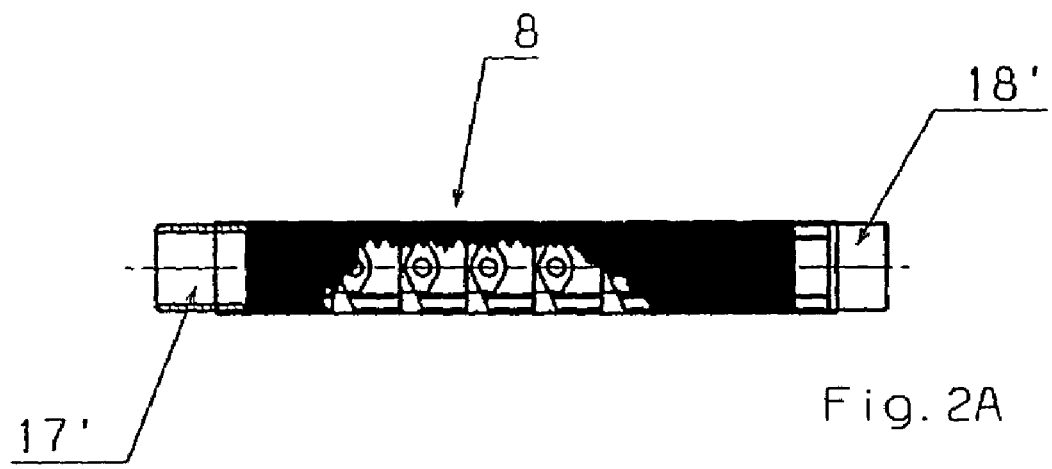
FIG. 2A shows a further enlarged view of the distal end of FIG. 1A, provided with a partly broken-away plastic sleeve in the form of a flexible tube.
Figure 2B:
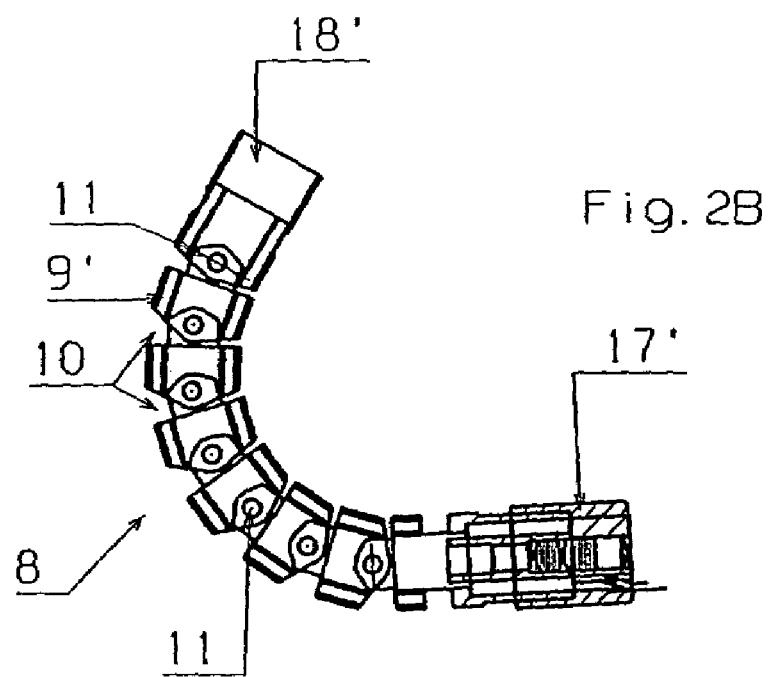
FIG. 2B shows a view of the distal end of FIG. 2A, but in a bent position.

The endoscope 1 shown in FIG. 1 consists essentially of a proximal portion 2, which is intended for handling and operation and comprises an eye-piece 3 and a hand-operating element 4, and further of a distal portion 5, which is intended for insertion into a body cavity, is provided as an insertion tube 6, and comprises a bendable portion 8 at its distal end 7. This bendable portion 8 differs from e.g. a flexible insertion tube 6 in that said portion is bendable in a controlled manner, i.e. it can be bent in desired directions by the hand-operating element 4, as shown in FIGS. 1A and 1B. Whereas the insertion tube 6 may be simply provided as a flexible plastic tube, this is not possible for the controllable, bendable portion, which needs to be produced, as shown in FIGS. 2A and 2B, from individual tube segments 9, which are adjustable relative to each other and can be adjusted in the desired direction via control wires 10, said tube segments 9 being pivotably connected with each other via connecting means 11.

In contrast to the above-described, known bendable portions of endoscopes, the tube segments 9 described in this embodiment example have a double-wall design, i.e. they consist of an outer tube segment 9' and an inner tube segment 9", respectively, which are identical with each other, except for the fact that they have different diameters and optionally also have different wall thicknesses and are easy to slide into each other.

Since these outer and inner tube segments 9' and 9" are substantially identical as regards their configuration, the design of one such tube segment will be first described hereinafter as exemplified by an outer tube segment 9', i.e. as exemplified by an outer bendable portion 8' of the insertion tube of the endoscope 1, which portion is formed by such tube segments 9'.

As is evident from FIGS. 5A to 5D and FIGS. 8 to 8D, the individual tube segments 9' comprise connecting means 11 protruding in an axial direction on their respective faces 12 and 13, said connecting means 11 having two different embodiments. Thus, the connecting means 11, which protrudes from the face 12 of a tube segment 9', is provided as a pin 14, cut out of the mantle 15' of the tube segment 9' in the manner of a circular disk.

In contrast thereto, the connecting means 11 provided on the opposite face 13 is provided as claws 16 embracing the pin 14, said claws being provided in pairs on the face 13. These claws 16 form a circular recess between them, which has the dimensions of the circular disk-shaped pin 14. These claws 16 are also cut out of the mantle 15' of the tube segment 9'. That is to say, the connecting means 11, be they provided as claws 16 or as pins 14, are located within the outer or inner periphery, respectively, of the bendable portion 8', i.e. they protrude neither inwardly nor outwardly and, thus, do not exceed the thickness of the mantle 15' of a tube segment 9' or of the bendable portion 8', respectively. As a consequence, both the inner wall and the outer wall of the bendable portion have smooth surfaces.

Merely the proximal and distal end portions 17' and 18', respectively, of the bendable portion 8' comprise correspondingly formed connecting means only on the respective faces facing the tube segments. The faces 21' and 22', respectively, which form the actual ends 19' and 20', respectively, do not comprise pin- and/or claw-type connecting means.

FIGS. 6A to 6B are corresponding representations of the inner bendable portion 8" for insertion into the outer bendable portion 8' of FIGS. 5A to 5D. Said portion 8" does not differ from the outer bendable portion 8' with respect to the design of its tube segments 9" and connecting means 11, but merely has a smaller outer diameter, which is almost equal to the inner diameter of the outer bendable portion 8'. This ensures that the inner bendable portion 8" can be slid into the outer bendable portion 8'.

However, the outer peripheral surface of the inner bendable portion 8" has at least two grooves 23 and 24, respectively, formed therein, which have a circumferential offset of 180° relative to each other and extend in an axial direction over the individual tube segments 9". The control wires 10, which are not shown, run in said grooves.

FIGS. 7A to 7D show the bendable portion 8, which consists of the outer bendable portion 8' and the inner bendable portion 8" inserted therein. In particular, FIG. 7B shows that the total length of the bendable inner portion 8" is slightly shorter than the total length of the outer bendable portion 8', which is due to the proximal and distal end portions 17" and 18", respectively, being shorter than the corresponding end portions 17' and 18', respectively, of the outer bendable portion 8'. This difference merely depends on purely constructional conditions which are related to the different functions of the end portions and do not play a role here.

FIGS. 8A to 8D show a single tube segment 9' of the outer bendable portion 8', from which the specific design of the respective pin- and claw-shaped connecting means 14 and 16, respectively, is evident. In order to allow the tube segments 9' to be arranged as closely behind each other as possible, i.e. without having to provide particularly great distances between them, the mantle 15' of the tube segment 9' has recesses 25 provided therein, into which the connecting means 11 of the opposite tube segment 9' protrude, said means being provided as claws 16.

FIG. 14 shows a bendable portion 8, which comprises nine tube segments and two end portions, namely the nine identical intermediate tube segments 9 and the respective end tube segments 17 or 18, respectively, and consequently, it comprises ten joints. The angles $\beta$ and $\beta^1$ as well as the distance a from pin to pin of two adjacent tube segments 9 may each be selected to be smaller and/or greater, thus changing the bendability of the bendable portion 8. The dimensions of these angles and distances may be determined as desired by the person skilled in the art.

The above-described embodiment of the bendable portion 8 is bendable in only one plane due to the connecting means 11 being respectively arranged with an offset of 180° between them and due to the presence of only two control wires arranged with a respective circumferential offset of 90° relative to said connecting means. However, it may also be desirable that the bendable portion should be bendable in a second plane, which is perpendicular to the first plane, thus ultimately enabling spatial movement of the bendable portion.

In this connection, an embodiment example is shown with reference to correspondingly designed tube segments of the outer and inner bendable portions in FIGS. 9 to 10D.

In these tube segments 109' and 109", respectively, the pins 114' or the claws 116', respectively, which are provided on the respective faces 112' and 113', respectively, are not located exactly opposite each other, but are offset 90° relative to each other over the periphery of the tube segment. Due to these connecting means 111' being arranged with an offset relative to each other from tube segment to tube segment only every second tube segment is adjustable in a first plane. The intermediate other tube segments can each be adjusted in the second plane. As for the rest, it can only be stated that the connecting means 111', i.e. the pins 114' and the claws 116' are of the same design as in the above-described first embodiment.

The tube segments 109" of the inner bendable portion 108" are illustrated in FIG. 10 to FIG. 10B, which show that, in addition to the axially extending grooves 123 and 124, respectively, which are located at 180° opposite each other, for the control wires moving the bendable portion in a first plane, there are provided two further grooves 123' and 124', which are each offset 90°, for the control wires bending the bendable portion in the second plane.

FIGS. 11A to 11D show the inner bendable portion 108", which is composed of the corresponding tube segments 109". The associated outer bendable portion, produced from the tube segments 109' shown in FIGS. 9 to 9C, is not depicted here.

This afore-described design, according to the invention, of a bendable portion at the distal end of an insertion tube of an endoscope, in contrast to the previously known bendable portions of such endoscopes, ensures a design with smooth walls, without protruding parts and without the use of individual turning pins. Moreover, providing the bendable portion with an outer and an inner bendable portion ensures particularly easy mounting of the control wires and, in addition, ensures that the interior space of the bendable portion has smooth walls and, therefore, does not make the incorporation of required additional components difficult.

The invention also provides a method of producing the afore-described bendable portions, said method being characterized in that, first of all, bending-resistant tubes 208' and 208", respectively, as shown in FIGS. 3 and 4, are provided, which respectively have the desired outer and inner diameters, depending on whether an inner bendable portion 8" or an outer bendable portion 8' is to be produced therefrom. If an inner bendable portion 8" is to be produced, the bending-resistant tube to be provided already comprises the axially extending grooves 23, 24, 23', 24', 123, 124, 123' and 124', which are required for the control wires.

Figure 12:
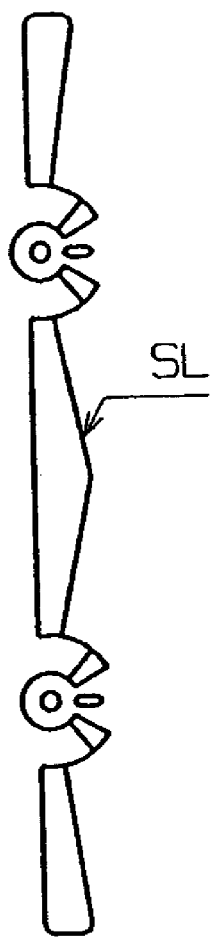
FIG. 12 shows the laser cutting-line in developed form.
Figure 13:
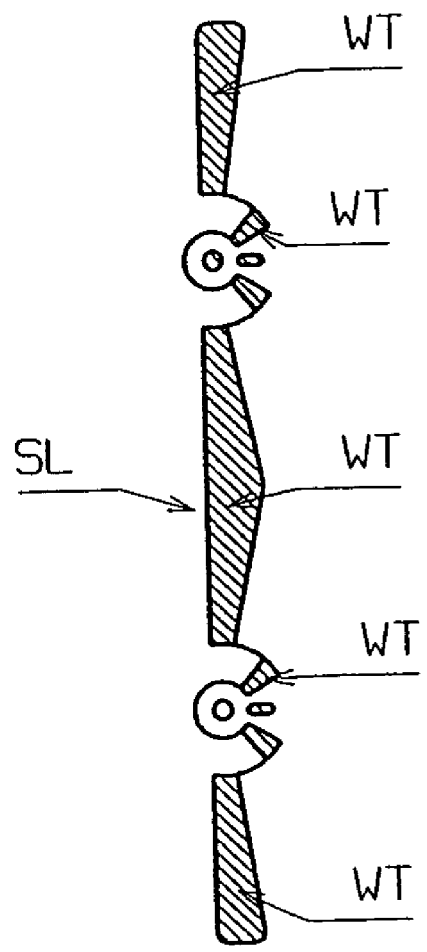
FIG. 13 shows the cut-out wall parts to be broken out of the tube.

Such bending-resistant tube 208' or 208", respectively, is placed in a laser-cutting device, with two alternatives being possible, namely that the tube is fixed and the laser-cutting device moves around the tube and can also be axially displaced relative to the tube, or that the laser-cutting device is arranged in a fixed position, and the bending-resistant tube can be both axially displaced and rotated. The laser-cutting device is programmed so as to either displace or rotate the tube relative to the laser beam, or the laser beam relative to the tube, in axial and radial directions, and the laser beam is guided on a cutting line SL, producing the portions which are shown in the Figures and which form the tube segments comprising the connecting means. FIG. 12 shows such a developed cutting line SL for guiding the laser, and FIG. 13 shows the wall parts WT, which are represented in shading and are cut out of the bending-resistant tube after effecting the laser cut on the cutting line shown in FIG. 12. Said wall parts are broken away either mechanically or by means of ultrasound.

Due to this laser-cutting technique, the desired bendable portion is produced from the initial bending-resistant tube, and it is ensured that the individual tube segments of the bendable portion cannot become detached from each other. This is because the laser beam is always aimed at the tube center axis of the bending-resistant tube, i.e. it is radially directed toward the tube. The cut surfaces SF shown in FIG. 8B, especially in the region of the pins 14 and the claws 16, are not parallel but form an angle between them. The individual parts of the connecting means, namely the pins and claws, could thus be displaced only radially outwardly. However, because the side of the tube segment located at 180° opposite is also provided with such connecting means, which can also be displaced only radially outwardly, the tube segments are secured against falling apart.

Although the present invention has been shown and described with respect to specific details of certain embodiments thereof, it is not intended that such details limit the scope of the invention other than as specifically set forth in the following claims, taking into consideration reasonable equivalents thereof.

The invention claimed is:

1. A bendable portion arranged proximate a distal end of an insertion tube of an endoscope, said bendable portion comprising:
an outer bendable portion including a plurality of outer tube segments, each of said outer tube segments having a mantle and including connecting parts which cooperate with the connecting parts of an adjacent one of the plurality of outer tube segments for a hinge-type connection, the connecting parts of each of the plurality of outer tube segments axially protruding from faces of each outer tube segments, the connecting parts for each outer tube segment being located within and not exceeding the thickness of the mantle of the respective outer tube segment;
an inner bendable portion-disposed within the outer bendable portion, the inner bendable portion including a plurality of inner tube segments, the plurality of inner tube segments numbering the same as the plurality of outer tube segments, each of said inner tube segments having a mantle and including connecting parts which cooperate with the connecting parts of an adjacent one of the plurality of inner tube segments for a direct hinge-type connection between the adjacent inner tube segments, the connecting parts of each of the plurality of inner tube segments axially protruding from faces of the inner tube segments, the connecting parts for each inner tube segment being located within and not exceeding the thickness of the mantle of the respective inner tube segments, said inner bendable portion including wherein four axially extending grooves provided on the outer peripheral surface of the inner bendable portion, the grooves being spaced circumferentially about the outer peripheral surface of the inner bendable portion at substantially 90°, each of said grooves having a control wire guided therein, the grooves of adjacent inner tube segments being held in alignment by the connecting parts between the inner tube segments,
wherein the connecting parts of at least one of the plurality of inner tube segments being arranged in a pair, a first member of the pair being located on a first of the faces of the at least one of the plurality of inner tube segments, a second member of the pair being located on a second of the faces of the at least one of the plurality of inner tube segments, said first of the faces being opposite said second of the faces, the first member of the pair being circumferentially offset at substantially 90° relative to the second member of the pair.

2. The bendable portion as claimed in claim 1, wherein the connecting parts provided on a first face of at least one of the plurality of outer tube segments is designed in the manner of a pin directed and protruding toward the face of the adjacent one of the plurality of outer tube segments, and wherein the connecting parts arranged on a second face of at least one of the plurality of outer tube segments is provided as claws embracing a pin of another adjacent one of the plurality of outer tube segment, both the pin and the claws of at least one of the plurality of outer tube segments being parts of the mantle of the respective outer tube segment.

3. The bendable portion as claimed in claim 1, wherein the connecting parts provided on one of the faces of a tube segment are provided either as a pin or as claws, in which case the connecting parts provided on the other face of the same tube segment are then either provided as claws or as a pin.

4. The bendable portion as claimed in claim 2, wherein the pin arranged on the first face of the at least one of the plurality of outer tube segments is designed in the manner of a circular disk and the claws provided on the face of the adjacent one of the plurality of outer tube segments enclose a circular recess between them, said recess having the dimensions of the circular disk-shaped pin, and wherein the claws accommodate the pin in said recess.

5. The bendable portion as claimed in claim 1, wherein the first tube segment at a proximal end of the inner and outer bendable portions and the last tube segment at a distal end of the inner and outer bendable portions have no pin-type or claw-type connecting parts on their faces forming the ends of the bendable portion.

6. The bendable portion as claimed in claim 1, wherein the individual tube segments of the inner and outer bendable portions are fixed to each other by spot welding in a state of complete congruence with each other.

7. The bendable portion as claimed in claim 1, wherein the individual tube segments of the inner and outer bendable portions are fixed to each other by spot welding in a state of complete congruence with each other.

* * * * *